(12) United States Patent
Gabel et al.

(10) Patent No.: US 6,780,171 B2
(45) Date of Patent: Aug. 24, 2004

(54) INTRADERMAL DELIVERY DEVICE

(75) Inventors: Jonathan B. Gabel, Randolph, NJ (US); Bradley M. Wilkinson, North Haledon, NJ (US); Charles G. Hwang, Ridgewood, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 200 days.

(21) Appl. No.: 10/112,757

(22) Filed: Apr. 2, 2002

(65) Prior Publication Data

US 2003/0187395 A1 Oct. 2, 2003

(51) Int. Cl.$^7$ ................................................ A61M 5/00
(52) U.S. Cl. ........................ 604/181; 604/244; 604/272
(58) Field of Search .................... 604/890.1, 19–22, 604/27, 30, 48, 93.01, 131, 132, 140, 141, 143, 145, 148, 151, 153, 154, 164.04, 164.08, 173, 174, 179–181, 185, 197, 200–205, 212, 239, 244, 246, 264, 272, 289, 294, 304–308

(56) References Cited

U.S. PATENT DOCUMENTS

| | | | |
|---|---|---|---|
| 3,814,097 A | | 6/1974 | Ganderton et al. |
| 3,964,482 A | | 6/1976 | Gerstel et al. |
| 4,601,707 A | * | 7/1986 | Albisser et al. .............. 604/131 |
| 4,645,486 A | * | 2/1987 | Beal et al. .................. 604/4.01 |
| 5,061,243 A | * | 10/1991 | Winchell et al. ............ 604/132 |
| 5,250,023 A | | 10/1993 | Lee et al. |
| 5,279,544 A | | 1/1994 | Gross et al. |
| 5,320,600 A | | 6/1994 | Lambert |
| 5,527,288 A | | 6/1996 | Gross et al. |
| 5,656,032 A | | 8/1997 | Kriesel et al. |
| 5,735,818 A | | 4/1998 | Kriesel et al. |
| 5,810,783 A | * | 9/1998 | Claro ......................... 604/199 |

(List continued on next page.)

FOREIGN PATENT DOCUMENTS

| | | | |
|---|---|---|---|
| CA | 2350307 | 1/2002 | |
| EP | 1 086 718 | 8/2000 | |
| GB | 2 221 394 | 2/1990 | |
| WO | WO 96/37256 | 11/1996 | |
| WO | WO 97/03718 | 2/1997 | |
| WO | WO 97/48440 | 12/1997 | |
| WO | WO 97/48441 | 12/1997 | |
| WO | WO 00/12173 | 3/2000 | |
| WO | WO 00/74766 | 12/2000 | |
| WO | WO 02/05889 A1 * | 1/2002 | .......... A61M/35/00 |
| WO | WO 02/05889 | 1/2002 | |

OTHER PUBLICATIONS

Mark R. Prausnitz, "Drug Delivery by Electrical, Ultrasonic, and Microneedle Disruption of Biological Barriers", Abstracts of Papers of the American Chemical Society, Mar. 26, 2000:219:176 MEDI.

(List continued on next page.)

Primary Examiner—Brian L. Casler
Assistant Examiner—Jennifer J Maynard
(74) Attorney, Agent, or Firm—Robert E. West (57) ABSTRACT

A delivery device for delivering a substance intradermally into the skin of a patient including a housing for contacting the surface of the skin and a disposable cartridge to be received in the housing. The cartridge includes an internal reservoir containing a substance to be delivered to the patient, a plurality of micro skin penetrating members and a fluid channel extending between the micro skin penetrating members and the reservoir. The housing includes a bottom wall with a central opening and a cover member. The cartridge is positioned in the housing with the micro skin penetrating members extending through the central opening of the bottom wall and positioned on the surface of the skin of a patient. The cover is closed onto the cartridge to dispense the substance from the cartridge through the micro skin penetrating members and into or through the skin of the patient.

14 Claims, 6 Drawing Sheets

U.S. PATENT DOCUMENTS

| | | | |
|---|---|---|---|
| 5,879,326 | A | 3/1999 | Godshall et al. |
| 5,997,501 | A | 12/1999 | Gross et al. |
| 6,050,988 | A | 4/2000 | Zuck |
| 6,083,196 | A | 7/2000 | Trautman et al. |
| 6,132,755 | A * | 10/2000 | Eicher et al. ............... 424/427 |
| 6,186,982 | B1 | 2/2001 | Gross et al. |
| 6,219,574 | B1 | 4/2001 | Cormier et al. |
| 6,230,051 | B1 | 5/2001 | Cormier et al. |
| 6,256,533 | B1 | 7/2001 | Yuzhakov et al. |
| 6,261,272 | B1 | 7/2001 | Gross et al. |
| 6,322,808 | B1 | 11/2001 | Trautman et al. |
| 6,611,707 | B1 * | 8/2003 | Prausnitz et al. ............. 604/21 |
| 2002/0006355 | A1 | 1/2002 | Whitson |

OTHER PUBLICATIONS

Devin V. Mcallister et al., "Microfabricated Microneedles For Gene And Drug Delivery", Annual Review of Biomedical Engineering, 2000, pp. 289/313.

Liwei Lin et al., "Silicon/Processed Microneedles", Journal of Microelectromechanical Systems, Mar. 1999, pp. 78/84, vol. 8, No. 1.

Ljubomir Ilic et al., "Microfabrication of Individual 200 $\mu$m Diameter Transdermal Microconduits Using High Voltage Pulsing in Salicylic Acid and Benzoic Acid", Journal of Investigative Dermatology, Jan. 2001, pp. 40/49, vol. 116, No. 1.

Sebastien Henry et al., "Microfabricated Microneedles: A Novel Approach to Transdermal Drug Delivery", Journal of Pharmaceutical Sciences, Aug. 1998, p. 922/925, vol. 87, No. 8.

John Brazzle et al., "Micromachined Needle Arrays for Drug Delivery or Fluid Extraction", IEEE Engineering in Medicine and Biology, Nov./Dec. 1999, pp. 53/58.

* cited by examiner

INTRADERMAL DELIVERY DEVICE

FIELD OF THE INVENTION

The present invention is directed to a method and a device for delivering a substance intradermally to a patient. The invention is further directed to a microneedle delivery device having a separable cartridge containing a unit dose of a substance for delivering the substance intradermally to a patient.

BACKGROUND OF THE INVENTION

Subcutaneous injection devices using a cannula that penetrates deep into the skin or muscle are effective for delivering a pharmaceutical or other substance to a patient. However, the pain normally induced by the cannula has prompted the development of less painful delivery methods. Recently, a number of intradermal devices have been designed in which microneedles are adapted to penetrate the skin to an intradermal depth at which a drug or pharmaceutical agent can be delivered to the patient and at which the microneedles do not cause pain or significant discomfort to the patient.

The skin is made up of several layers, with the upper composite layer being the epithelial layer. The outermost layer of the skin, the stratum corneum, has well known barrier properties to prevent molecules and various substances from entering the body and analytes from exiting the body. The stratum corneum, which is a complex structure of compacted keratinized cell remnants having a thickness of about 10–30 microns, forms a waterproof membrane to protect the body from invasion by various substances and the outward migration of various compounds.

The natural impermeability of the stratum corneum prevents the administration of most pharmaceutical agents and other substances through the skin. Numerous methods and devices have been proposed to enhance the permeability of the skin and to increase the diffusion of various drugs through the skin for utilization by the body. Typically, the delivery of drugs through the skin is enhanced by increasing either the permeability of the skin or the force or energy used to direct the drug through the skin.

Delivering various substances through the skin is also attained by forming micropores or cuts through the stratum corneum. By piercing the stratum corneum and delivering a drug to the skin in or below the stratum corneum, many drugs can be administered effectively. In a similar manner, some substances can be extracted from the body through cuts or pores formed in the stratum corneum. The devices for piercing the stratum corneum generally include a plurality of micron-sized needles or blades having a length selected to pierce the stratum corneum without passing completely through the epidermis. Examples of these devices are disclosed in U.S. Pat. No. 5,879,326 to Godshall et al.; U.S. Pat. No. 5,250,023 to Lee et al., and WO 97/48440.

In some of above-noted samples micron-sized needles or blades deliver substances to the body by allowing the substance to diffuse through the pores or channels in the device. Many of these prior art devices do not provide a controlled delivery of a substance to the patient.

The prior methods and devices for the intradermal administration of substances have had limited success. Accordingly, a continuing need exists in the industry for an improved device for the administration of various drugs and other substances to the body.

SUMMARY OF THE INVENTION

The present invention is directed to a device for the intradermal delivery of a fluid substance through the skin of a patient. In particular, the invention is directed to a device having a separable cartridge containing a fluid substance, such as a drug or vaccine, and for delivering the substance below the stratum corneum of the skin to a depth at which the substance can be absorbed and utilized by the body.

The delivery device of the invention includes a housing for engaging the surface of the skin and a dispensing cartridge received within the housing for dispensing and delivering the substance to the patient. The housing is provided with a coupling member, such as a wrist strap, for holding the housing in engagement with the skin of the patient.

The cartridge defines an internal reservoir containing the substance to be delivered to the patient and at least one skin penetrating member is provided for delivering the substance intradermally to the patient. A fluid channel extends between the reservoir and the skin penetrating member. In the preferred embodiment, a plurality of skin penetrating members are provided in an array to deliver the substance intradermally to the patient. In the illustrated embodiments the skin penetrating members are an array of hollow microneedles. The cartridge includes a diaphragm or seal in the fluid channel to contain the substance within the cartridge reservoir. The cartridge includes a piercing member for piercing the seal and allowing the fluid substance to flow from the reservoir through the fluid channel to the skin penetrating members for delivery to the patient. The housing includes a hinged cover member with a cam positioned to contact and actuate the piercing member when the cover member is closed. The cover member is provided with a spring member to apply pressure to the cartridge and to the fluid substance when the cover member is closed. The pressure applied to the fluid causes it to flow through the fluid channel and the needles to be delivered intradermally to the patient. An indicator window can be provided in the cover member to provide an indication of when the cartridge is empty and the dispensing is complete.

Accordingly, a primary object of the invention is to provide an intradermal delivery device having a separable and disposable cartridge containing a substance and at least one skin penetrating member for delivering the substance to the patient.

A further object of the invention is to provide a device for penetrating the skin and delivering a unit dose of a substance through the skin substantially without pain to the patient.

Another object of the invention is to provide a device having a plurality of microtubes, needles, microneedles, blades or lancets for piercing the stratum corneum of the skin to a depth sufficient for delivering a substance through the skin of a patient.

A further object of the invention is to provide a delivery device having at least one skin penetrating member and including a cartridge having a collapsible chamber for containing a fluid substance to be delivered to a patient via the skin penetrating member.

Another object of the invention is to provide a cartridge for use with an intradermal delivery device wherein the cartridge is collapsible to permit application of a dispensing pressure to the fluid substance in the cartridge for delivering the substance intradermally to the patient.

Another object of the invention is to provide a device for delivering a substance to a patient wherein the device has a dispensing member in the form of a spring cooperating with a cartridge and an internal supply channel connecting a reservoir in the cartridge to at least one skin penetrating member for delivering the substance to the patient.

A further object of the invention is to provide a delivery device having a cartridge with at least one flexible or elastic wall that can be deflected inwardly to dispense a substance from a reservoir through a skin penetrating member for delivery to the patient.

Another object of the invention is to provide an intradermal delivery device including a cartridge having an internal chamber with a fluid outlet, a diaphragm, and a piercing member for piercing the diaphragm for delivering a substance to a patient.

These and other objects of the invention are substantially attained by providing an intradermal delivery device comprising a housing having an internal cavity dimensioned to receive a cartridge. The cartridge includes at least one skin penetrating member, and a channel providing fluid communication between a reservoir in the cartridge and the skin penetrating member.

The objects and advantages of the invention are further attained by providing an intradermal delivery device comprising a housing and a cartridge removably received in the housing. The cartridge has an internal reservoir containing a fluid substance to be delivered to the patient. The device includes at least one skin penetrating member which has a length sufficient to penetrate the surface of the skin of a patient. The skin penetrating members can be placed in fluid communication with the cartridge for delivering the substance in the cartridge to the patient.

A yet further object of the invention is attained by providing an intradermal delivery device which comprises a housing having a coupling member for attaching the housing to the surface of the skin of a patient. A cartridge is removably received in the housing. The cartridge has an internal reservoir containing a fluid substance to be delivered to a patient. The cartridge has at least one flexible wall. A dispensing member deflects the flexible wall inwardly with respect to the cartridge for dispensing the substance from the cartridge. At least one skin penetrating member is in fluid communication with the cartridge for delivering the substance from the cartridge to the patient.

The objects, advantages, and other salient features of the invention will become apparent from the following detailed description, which, in conjunction with the accompanying drawings, discloses preferred embodiments of the invention.

DETAILED DESCRIPTION OF THE EMBODIMENTS

The present invention is directed to an intradermal device and to a method for delivering a fluid substance in or through the skin of a patient. More particularly, the invention is directed to an intradermal delivery device for administering a substance into or below the stratum corneum of the skin of a patient to a depth sufficient for the substance to be absorbed and utilized by the body.

As used herein, the term penetrate refers to entering a layer of the skin without necessarily passing completely through the layer. Piercing refers to passing completely through the element or layer being pierced.

The device in one embodiment of the present invention is suitable for use in administering various substances, including pharmaceutical agents, to a patient, and particularly to a human patient. As used herein, a pharmaceutical agent includes a substance having biological activity that can be delivered through the body membranes and surfaces, particularly the skin. Examples include antibiotics, antiviral agents, analgesics, anesthetics, anorexics, antiarthritics, antidepressants, antihistamines, anti-inflammatory agents, antineoplastic agents, vaccines, including DNA vaccines, and the like. Other substances that can be delivered intradermally to a patient include proteins, peptides or fragments thereof. The proteins and peptides can be naturally occurring, synthesized or recombinantly produced.

FIGS. 1–15 illustrate a preferred embodiment of the invention for delivering a substance through the skin of a patient. The device of the invention is constructed to penetrate selected layers of the dermis of a patient to attain the desired depth of penetration. The desired depth of penetration is determined by the substance being delivered and the desired rate of absorption by the body. When the substance being delivered is a pharmaceutical agent, the device is provided with micro skin penetrating members each having a length to pierce the stratum corneum substantially without penetrating the layers of the dermis below the stratum corneum. By delivering a substance just below the stratum corneum, the substance can be absorbed and utilized by the body substantially without pain or discomfort to the patient. Preferably, the skin penetrating members have a length to penetrate the skin to a depth at which the patient experiences little or no pain.

Figure 1:
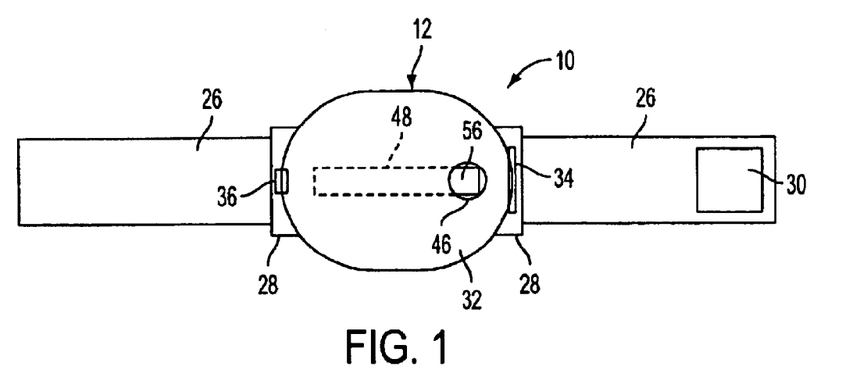
FIG. 1 is a top view of the delivery device in accordance with an embodiment of the invention.
Figure 2:
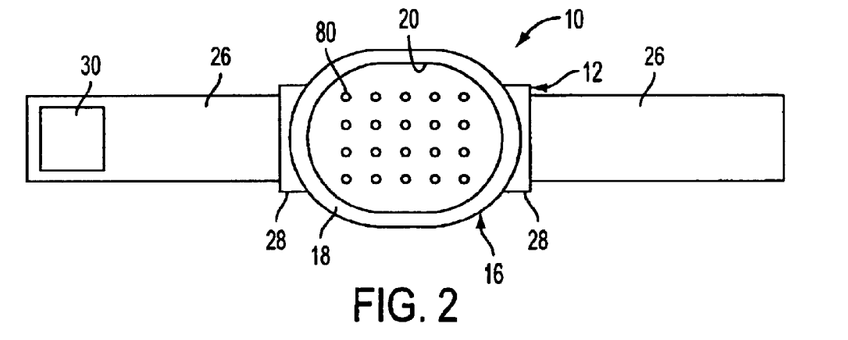
FIG. 2 is a bottom view of the device of FIG. 1.
Figure 3:
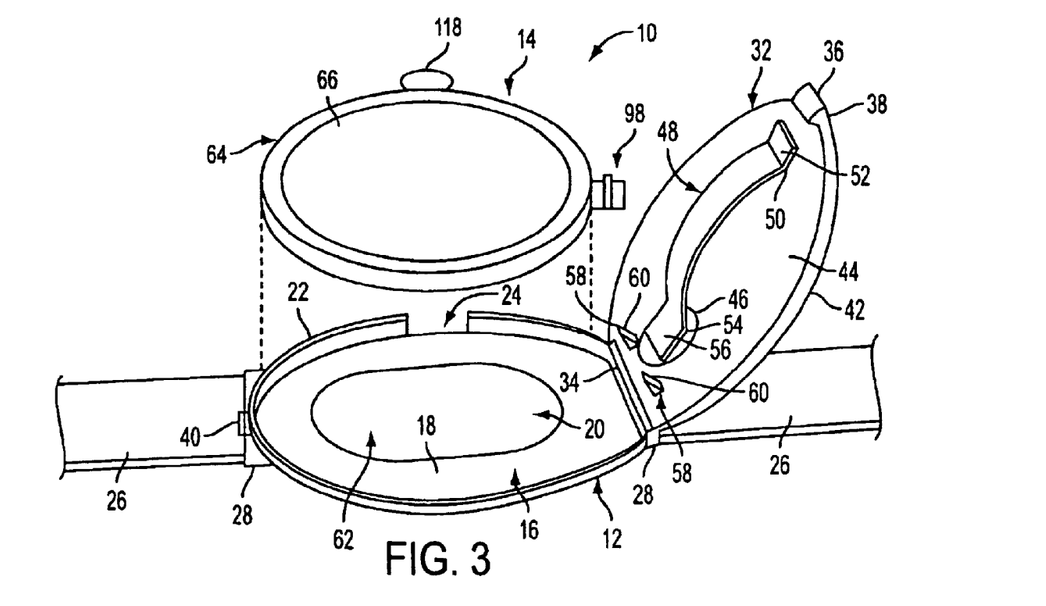
FIG. 3 is a perspective exploded view of the device of FIG. 1 showing the cover in the open position.

As shown in FIGS. 1–3, the delivery device of the invention is designated generally by the reference number 10. The delivery device 10 includes a housing 12 and a cartridge 14 for delivering a substance intradermally to a patient. In a preferred embodiment of the invention, the device 10 is a small compact device adapted to be attached to the surface of the skin during delivery of the substance. Typically, the device 10 will have dimensions suitable for attachment to the wrist or arm of the patient.

The housing 12 includes a base 16 with a generally oval shape. Alternatively, the base 16 can be round, square or rectangular, as desired. The base 16 comprises a bottom wall 18 defining a central opening 20. A side wall 22 is coupled to bottom wall 18 and extends upwardly around the peripheral edge of bottom wall 18 to define the lower part of an internal cavity. As shown in FIG. 3, side wall 22 includes a notched portion 24 to accommodate cartridge 14 as described in greater detail hereinafter.

In the illustrated embodiment, base 16 includes a coupling member for coupling device 10 to the skin of the patient. In this embodiment, the coupling member is a strap 26 coupled to opposite ends 28 of base 16. Strap 26 is sufficiently flexible to conform to the surface of the skin for attaching device 10 to the patient. Typically, strap 26 is constructed similarly to a watch band so that device 10 can be strapped to the wrist or arm of a patient like a watch. Strap 26 preferably includes coupling members 30 such as hook and loop fasteners at the outer ends for coupling the ends together and securing the device to the wrist of the patient. In alternative embodiments, strap 26 can include a buckle, snap, adhesive or other fastener capable of attaching device 10 to the skin of a patient in a desired location.

Housing 12 also includes a cover 32 connected to base 16 by a hinge 34 so that cover 32 can pivot between an open position and a closed position. In the illustrated embodiment, hinge 34 is positioned at one end 28 of base 16. Hinge 34 can be integrally formed with base 16 and cover 32 to form a living hinge. Alternatively, hinge 34 can be formed by cylindrical portions coupled together by a hinge pin. In alternative embodiments, cover 32 can be hinged to base 16 along a side edge as desired. The cover 32 may also be coupled to base 16 by a snap, interference or friction fit.

Cover 32 has a shape and dimensions complementing base 16 to mate with side wall 22 and close the open top side of base 16. Preferably, cover 32 includes a coupling tab 36 at an outer end 38 for latching cover 32 in a closed position. Preferably, side wall 22 of base 16 includes a coupling tab 40 for coacting with coupling tab 36 of cover 32. Typically, coupling tabs 36 and 40 include complementary lips for making an interference fit to hold the cover 32 in a closed position.

Cover 32 includes a top side 42 and a bottom side 44 with the bottom side 44 facing inwardly toward base 16. As shown in FIG. 1, cover 32 includes a window 46 made of a transparent or translucent material. In the illustrated embodiment, window 46 is positioned adjacent to the hinge 34.

The cover 32 functions to cause a fluid substance within the cartridge to be dispensed when the cover is closed. The cover includes a spring 48 to apply pressure to cartridge 14. Spring 48 is preferably a leaf spring member having an arcuate shape capable of applying pressure to cartridge 14 and to the substance within the cartridge through the cartridge wall. Spring 48 has a first end 50 with a substantially straight tab 52 extending longitudinally with respect to spring 48. Spring 48 includes a second end 54 having a second tab 56 oriented in substantially the same plane as first tab 52. As shown in FIG. 3, first tab 52 of spring 48 is fixed to bottom face 44 of cover 32. Spring 48 is oriented on bottom face 44 so that second tab 56 is positioned to be viewed through window 46 when spring 48 is in its normal relaxed condition. Second tab 56 is free to slide along bottom face 44 as spring 48 is stressed by being flexed toward the bottom face 44. In an alternative embodiment, a coil spring on the cover bottom face 44 could be employed to apply a downward pressure on cartridge 14.

At least one and typically two cam members 58 are mounted on bottom face 44 of cover 32 as shown in FIG. 3. Cam members 58 each have an inclined camming surface 60 extending outwardly from bottom face 44. As shown in FIG. 3, cam members 58 are positioned adjacent hinge 34 for engaging cartridge 14 as described hereinafter in greater detail.

Figure 4:
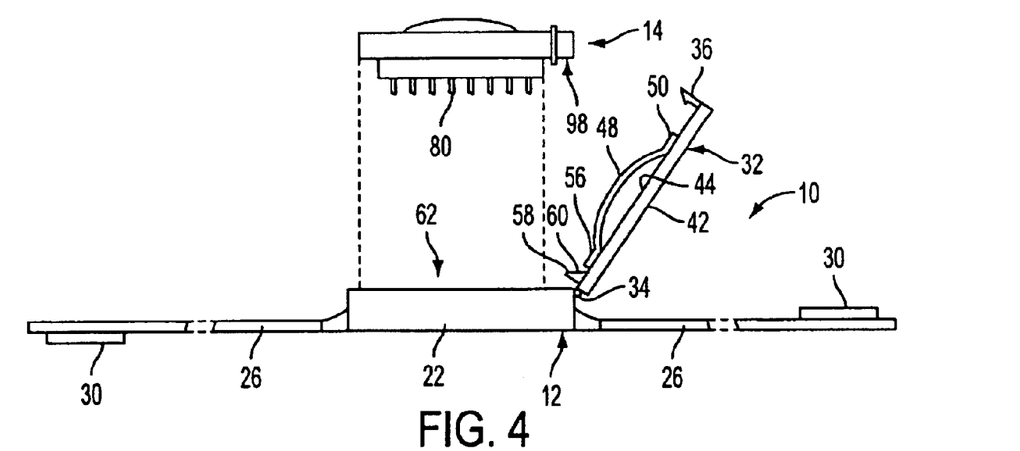
FIG. 4 is an exploded side view of the housing and cartridge of FIG. 1 showing the skin penetrating members extending below the cartridge.
Figure 5:
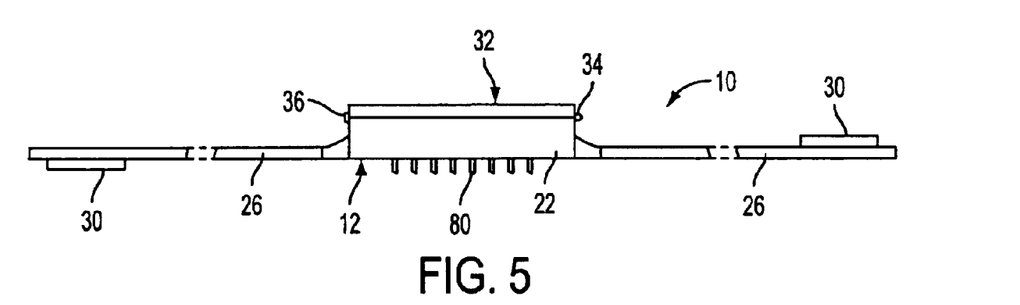
FIG. 5 is a side view of the assembled housing and cartridge showing the skin penetrating members extending below the housing.

Cover 32 and base 16 define an internal cavity 62 dimensioned to receive cartridge 14. As shown in FIGS. 4 and 5, cartridge 14 is placed in the lower portion of cavity 62 defined by base 16 so that cover 32 can be pivoted to the closed position to enclose cartridge 14 in cavity 62.

Figure 6:
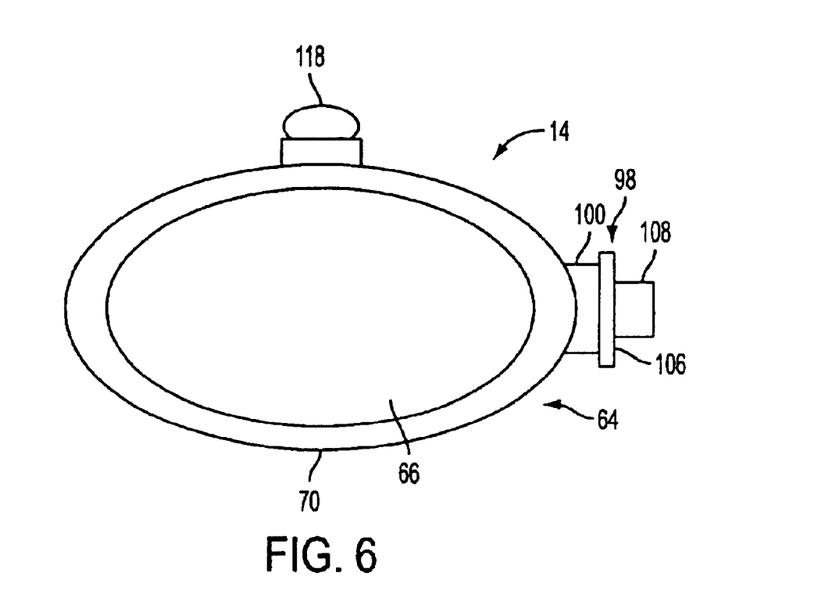
FIG. 6 is an enlarged top view of the cartridge of the embodiment of FIG. 1.
Figure 7:
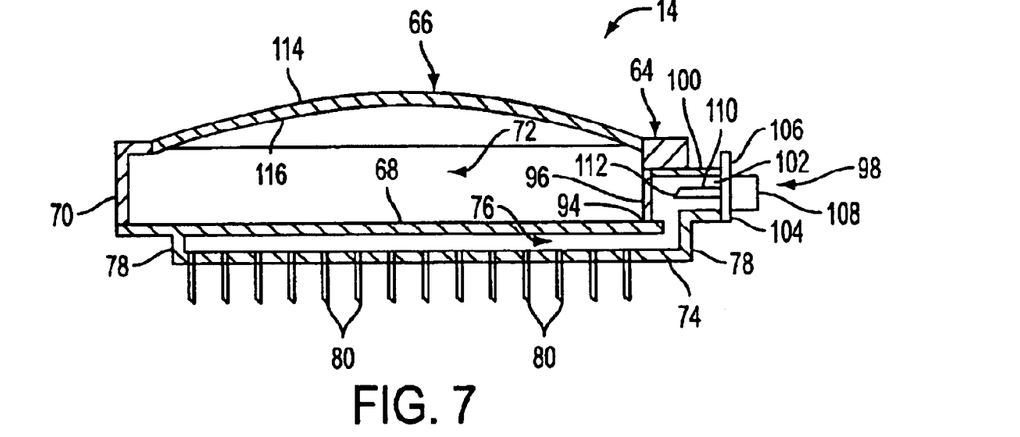
FIG. 7 is a sectional side view of the cartridge showing the internal reservoir, flexible top wall, channel, seal and piercing members with the reservoir being shown filled with a substance to be delivered to a patient.

As shown in FIGS. 6–7, cartridge 14 has a shape and size to fit within cavity 62. In the illustrated embodiment, cartridge 14 has a generally oval shape corresponding to the shape of housing 12. Cartridge 14 includes a body 64 having a top wall 66, a bottom wall 68 and a side wall 70. Side wall 70 extends in a generally perpendicular direction between top wall 66 and bottom wall 68 and defines an internal reservoir 72. Reservoir 72 in preferred embodiments is dimensioned to contain a unit dose of a substance to be delivered to the patient. Preferably, side wall 70 forms a fluidtight seal between top wall 66 and bottom wall 68 to form reservoir 72 for containing the substance to be delivered to the patient. Alternatively, cartridge 14 can be made having the top wall and the bottom wall joined together about their peripheral edges.

Cartridge 14 also comprises a lower outer wall 74 spaced from bottom wall 68 to define a fluid channel 76. Preferably, outer wall 74 is connected to bottom wall 68 by a side wall 78 for spacing outer wall 74 from bottom wall 68. Preferably, outer wall 74 and sidewall 78 are shaped and sized to fit into central opening 20 of base 16 so that outer wall 74 is oriented generally in the same plane as bottom wall 18 of base 16 when cartridge 14 is assembled in housing 12. The periphery of the outer wall 74 lies within the periphery of the bottom wall 68 so that when the cartridge is assembled in the housing 12 with the bottom wall 74 and sidewall 78 received in opening 20, the outer portion of the bottom wall 68 will engage and be supported by bottom wall 18 of the base 16.

Outer wall 74 supports one or more skin penetrating members 80. In some embodiments, skin penetrating members are arranged in an array of rows and columns spaced apart by a substantially uniform distance. The actual length and spacing of skin penetrating members 80 can depend on the substance being delivered and the delivery site on the patient. Typically, skin penetrating members 80 are needles projecting from outer wall 74. Skin penetrating members 80 are arranged in an array designed to deliver an effective amount of a substance through the skin of a patient over a selected period of time. Typically, the needle array has an area of about 1 cm$^2$ to about 10 cm$^2$, and preferably about 2–5 cm$^2$.

Figure 10:
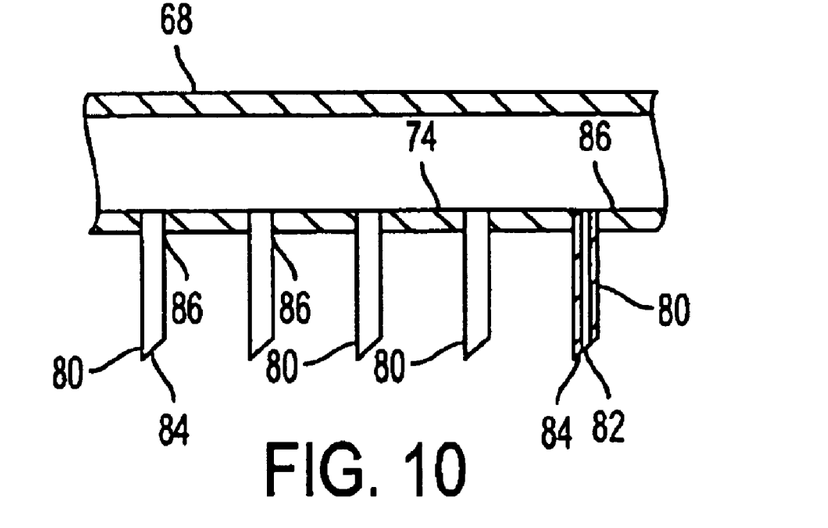
FIG. 10 is a partial sectional side view of the needle array in a preferred embodiment.

As shown in FIG. 10, skin penetrating members 80 are hollow needles each having an axial passage 82 and a beveled sharp outer tip 84 for piercing the skin of the patient. Skin penetrating members 80 are mounted in apertures 86 in outer wall 74 so that axial passages 82 are in fluid communication with fluid channel 76. Skin penetrating members 80 can be fixed to outer wall 74 by a suitable adhesive or a press fit into apertures 86. In an alternative embodiment shown in FIG. 11, micro skin penetrating members 88 can be formed as one piece with outer wall 74. In the embodiment illustrated in FIG. 11, skin penetrating members 88 each have a beveled sharp tip 90 and an axial passage 92 extending between beveled tip 90 and outer wall 74 for fluid communication with fluid channel 76.

As shown in FIG. 7, side wall 70 of body 64 includes an outlet opening 94 closed by a seal member 96. Seal member 96 is preferably made of an easily pierced plastic material and coupled to side wall 70 to form a fluidtight seal over opening 94. A piercing assembly 98 is mounted in side wall 78 adjacent to seal 96 and fluid channel 76. In the embodiment illustrated, piercing assembly 98 comprises a hollow sleeve 100 having a substantially cylindrical shape and an axial passage 102. Sleeve 100 extends outwardly from seal 96 to an outer end 104. A rib 106 extends outwardly from the outer surface of sleeve 100 for orienting cartridge 14 in housing 12. A reciprocating plunger 108 having a piercing member 110 in the form a needle is mounted in axial passage 102 of sleeve 100. Plunger 108 can move from a first outer position shown in FIG. 7 to an inward position shown in FIG. 8. Piercing member 110 has a length so that its tip 112 is spaced from seal member 96 when plunger 108 is positioned outwardly in sleeve 100. Plunger 108 can be forced inwardly through sleeve 100 so that tip 112 of piercing member 110 pierces seal member 96 to provide fluid communication between reservoir 72 and fluid channel 76.

In preferred embodiments, bottom wall 68 and side wall 70 are formed from a substantially rigid material to maintain the structural integrity and shape of cartridge 14. Top wall 66 of cartridge 14 is made from a flexible material so that top wall 66 can be depressed inwardly to dispense the contents of reservoir 72 through fluid channel 76 and skin penetrating members 80. Preferably, top wall 66 is made of a flexible plastic material that is sealed to side wall 70 to form a fluidtight enclosure.

Figure 8:
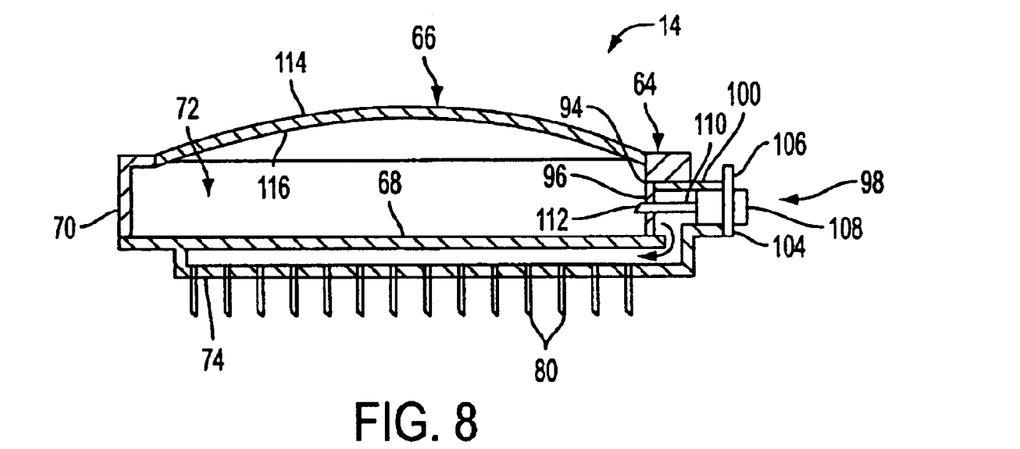
FIG. 8 is a sectional side view of the cartridge of FIG. 7 showing the piercing member piercing the seal.
Figure 9:
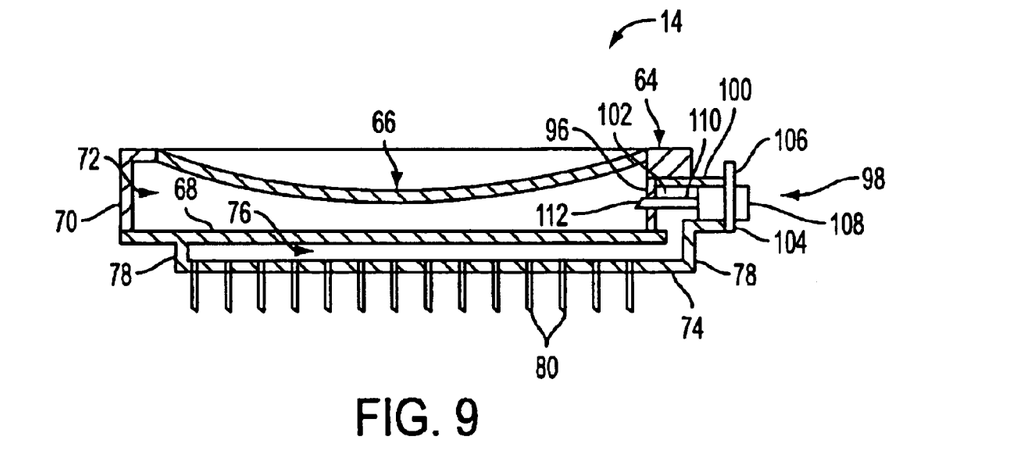
FIG. 9 is a sectional side view of the cartridge of FIG. 7 showing the action of the cartridge to dispense the substance.

In the embodiment illustrated, top wall 66 has a substantially dome shape having a convex outer surface 114 and a concave inner surface 116. In alternative embodiments, top wall 66 can be substantially flat in a normal position and oriented in a plane with the top edge of side wall 70. As shown in FIGS. 7–9, piercing assembly 98 can be actuated to cause piercing member 110 to pierce seal 96 as shown in FIG. 8. Top wall 66 can then be pressed downwardly by a mechanical pressure to dispense the substance in cavity 72 through the opening formed by piercing member 110 into fluid channel 76. The mechanical pressure on top wall 66 provides a dispensing pressure to the fluid in the reservoir 72 to force the fluid through channel 76 and through skin penetrating members 80 into or through the skin of the patient.

Figure 12:
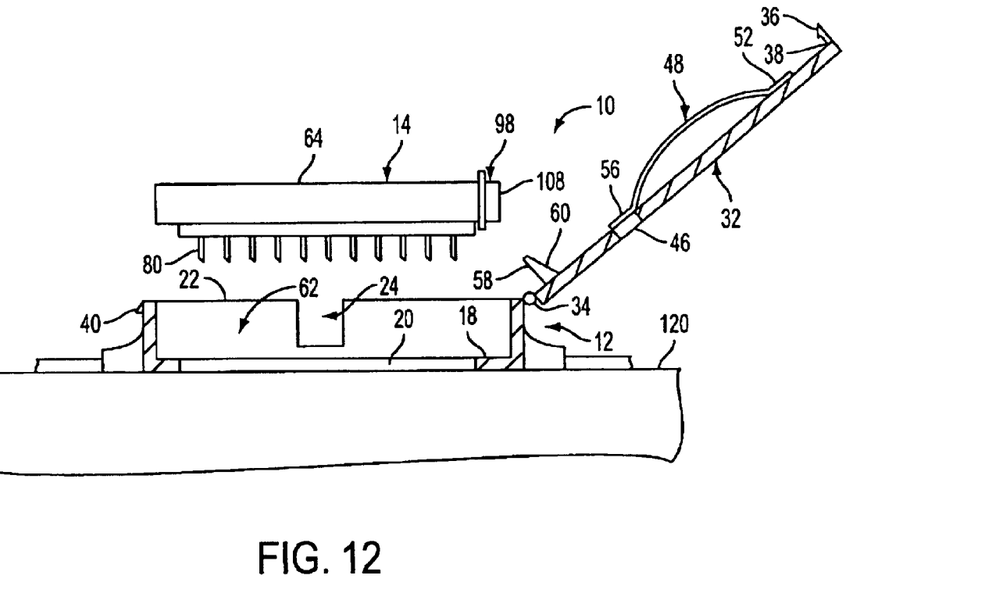
FIG. 12 is an exploded sectional side view of the device showing the housing and the cartridge.
Figure 13:
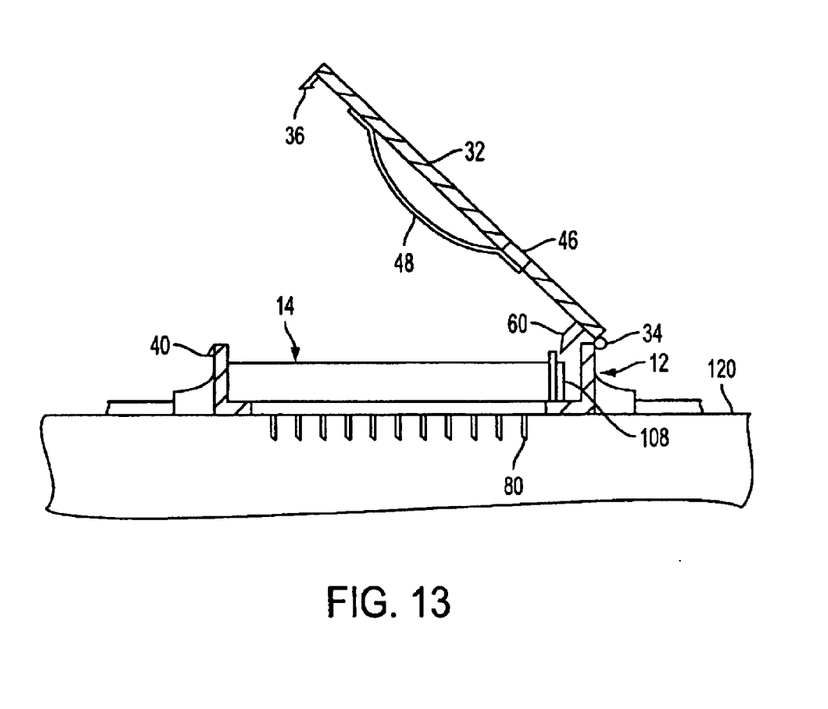
FIG. 13 is a sectional side view of the delivery device of FIG. 12 showing the cartridge received in the housing with the cover open.
Figure 14:
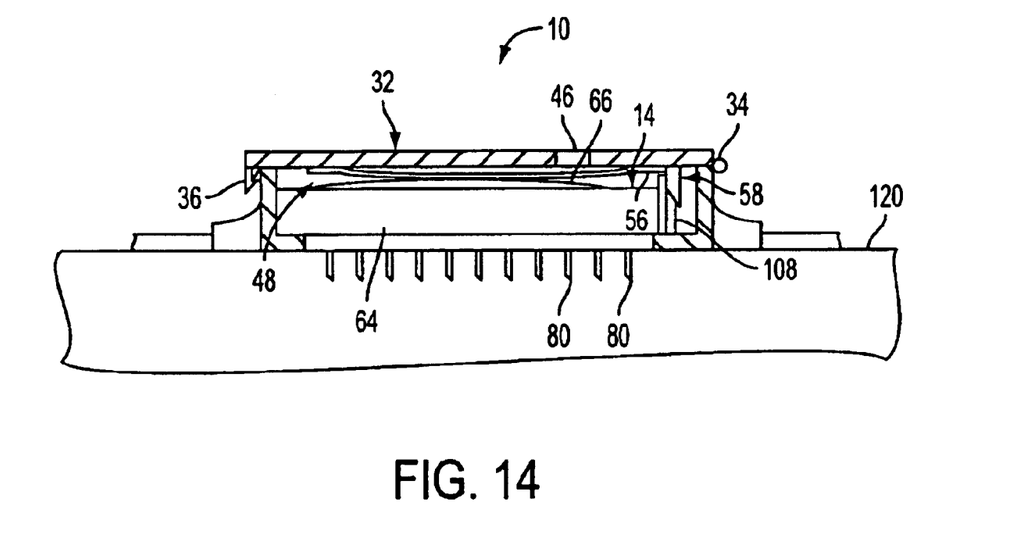
FIG. 14 is a sectional side view of the device of FIG. 13 showing the cover member in the closed position in which cam members actuate a piercing member and a spring applies a dispensing pressure to the cartridge.

In the illustrated embodiment of the invention as shown in FIG. 6, cartridge 14 includes a tab 118 positioned on side wall 70 to handle and manipulate cartridge 14. Tab 118 is preferably dimensioned to be gripped by the user for handling cartridge 14 without contacting skin penetrating members 80. Device 10 is assembled by positioning cartridge 14 in housing 12 with tab 118 received in notch 24 of side wall 22 and with skin penetrating members 80 extending through opening 20 in bottom wall 18 of base 16. Cartridge 14 is oriented in housing 12 so that piercing assembly 98 is positioned adjacent to hinge 34 to be activated by cam members 58 as shown in FIGS. 12 and 13. Cover 32 is then pivoted on hinge 34 to the closed position so that cam members 58 engage plunger 108 of piercing assembly 98. As shown in FIGS. 13 and 14, inclined camming surfaces of cam member 58 engage plunger 108 and move plunger 108 inwardly until piercing member 110 pierces seal 96. The device 10 should be positioned on the surface of the skin 120 of a patient in the desired target area so that skin penetrating members 80 pierce the surface of skin 120 before cover 32 is pivoted to the closed position.

Cover 32 is pivoted to the closed position shown in FIG. 14 so that spring member 48 engages top wall 66 of body 64 of cartridge 14. Cover 32 is latched in the closed position with coupling tabs 36 and 40 mating together to hold cover 32 in the closed position so that spring 48 is stressed and applies dispensing pressure against top wall 66 and to the fluid within the reservoir 72. As shown in FIG. 14, reservoir 72 of body 64 is initially filled with a fluid to be delivered to the patient so that top wall 66 bulges outwardly from body 64. Spring 48 contacting top wall 66 is initially flattened such that second end 54 and second tab 56 of spring 48 slide away from the fixed end of spring 48 radially outward with respect to cover 32 toward hinge 34. At this point in the dispensing process, as shown in FIG. 14, second tab 56 is positioned outwardly from window 46 and is no longer visible through window 46. The second tab 56 can include a color indicator or other suitable indicia visible through window 46.

Figure 15:
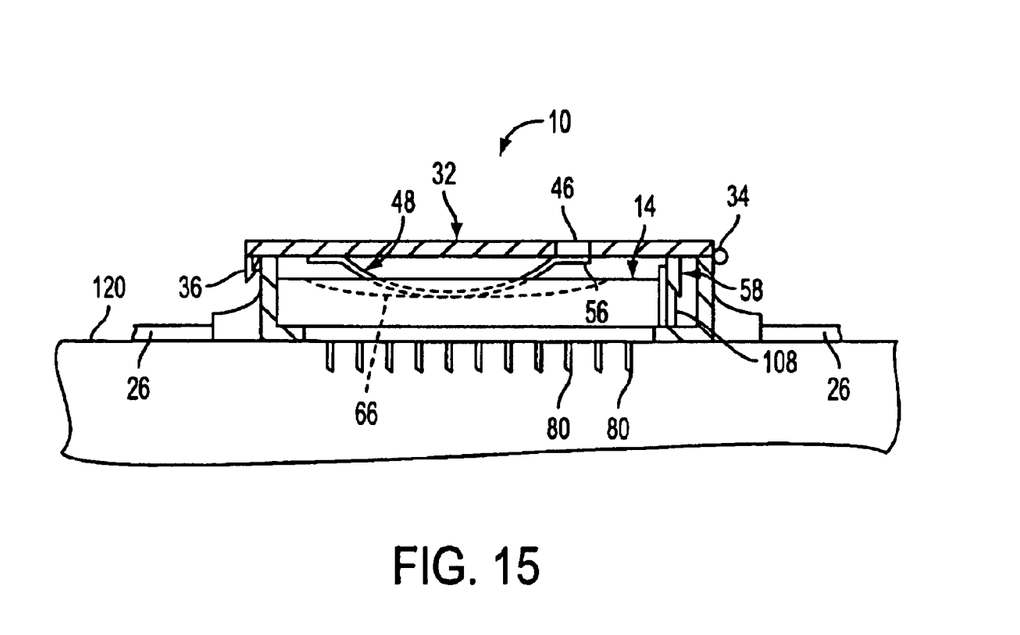
FIG. 15 is a sectional side view of the device of FIG. 13 showing the spring dispensing the substance from the cartridge.

Spring 48 provides a substantially constant and uniform pressure against top wall 66, thereby providing a dispensing pressure to the fluid in reservoir 72. Preferably, spring 48 applies a downward pressure on cartridge 14 to dispense the contents at a rate and pressure such that the fluid can be delivered through the skin with minimal leakage around each of the micro skin penetrating members. As the fluid in reservoir 72 is dispensed through fluid channel 76 and skin penetrating members 80 into the skin of the patient, top wall 66 is deflected inwardly into the reservoir 72. As shown in FIG. 15, spring 48 eventually resumes its original shape so that second tab 56 slides back into position below window 46. Second tab 56 being visible through window 46 provides an indication that the substance has been dispensed from reservoir 72 so that the operator will know that the delivery step is complete. At the end of the delivery step, cover 32 can be opened and cartridge 14 removed and discarded. The spent cartridge can be replaced with a fresh cartridge for delivering a substance to the patient by repeating the process.

Cartridge 14 is typically constructed and manufactured as a single use disposable member. Cartridge 14 is illustrated as being made as a unitary, integrally formed unit. In other embodiments, cartridge 14 can be made from various molded elements that are assembled and coupled together in a suitable manner to form cartridge 14.

Housing 12 is also typically made of a suitable plastic material. In one embodiment, base 16 and cover 32 are made as separate elements and coupled together by hinge 34. In alternative embodiments, base 16 and cover 32 can be molded as a single unit connected together by a flexible portion to comprise the hinge 34. Housing 12 and cartridge 14 are typically made of a non-reactive plastic material. Suitable plastic materials include polyethylene, polypropylene, polyesters, polyamines, polycarbonates, and copolymers thereof.

Skin penetrating members 80 preferably have a length suitable to achieve the desired depth of penetration in the skin. The length and thickness of the skin penetrating members are selected based on the substance being administered and the thickness of the skin and the target location where the device is applied. In embodiments of the invention, the skin penetrating members can be microneedles, microtubes, solid or hollow needles, lancets, and the like. In one preferred embodiment, skin penetrating members 80 are stainless steel hollow needles or cannulas. The needles are generally about 24 gauge to 50 gauge, and preferably about 30 gauge to about 36 gauge needles, and more preferably about 34 gauge. Smaller needles penetrate the surface of the skin more easily than larger needles and are generally preferred. The needles are mounted in outer wall 74 to provide an effective length of about 50 microns to about 5000 microns. In one embodiment, the needles are fixed to the base to provide an effective length of about 500 microns to about 3000 microns. In other embodiments, the needles can have an effective length ranging between about 1000 microns and 2000 microns. Typically, the needles have an effective length of about 500 microns to about 1000 microns.

Figure 11:
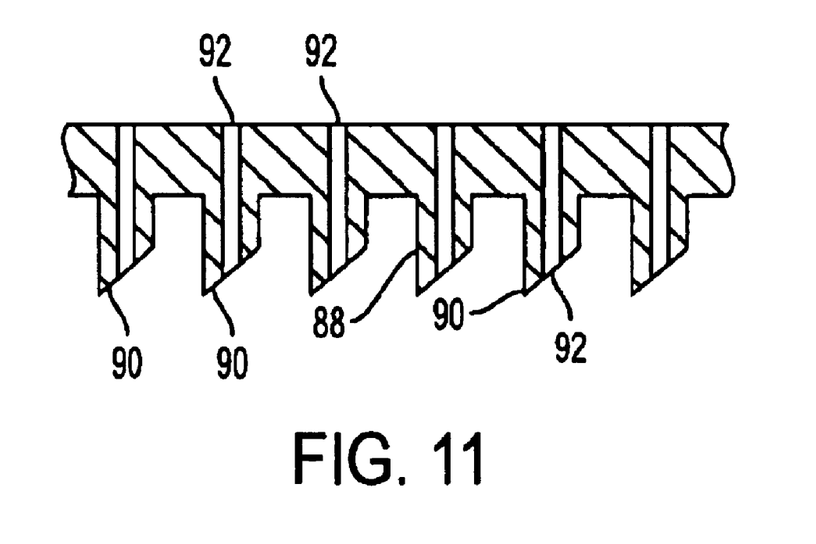
FIG. 11 is a partial sectional side view of the needle array in an alternative embodiment of the invention.

In the embodiment shown in FIG. 11, the skin penetrating members are integrally formed with the outer wall and are arranged in an array of spaced-apart rows and columns, although there can be just one skin penetrating member or a few. The needle array can be manufactured from a silicon wafer that is machined and etched to form the individual needles. In alternative embodiments, the needle array can be made of stainless steel, tungsten steel and alloys of nickel, molybdenum, chromium, cobalt and titanium. In further embodiments, the needle array can be formed from ceramic materials, glass, polymers and other non-reactive materials. In embodiments in which the needles are integrally formed with the outer wall, the needles generally have an effective length of about 50 microns to about 1000 microns and a diameter of about 50 microns to about 100 microns.

The array of micro skin penetrating members is typically arranged in rows and columns but the skin penetrating members can be arranged in other suitable patterns. Preferably, the skin penetrating members are spaced sufficiently apart to enable the skin penetrating members to penetrate the skin to a substantially uniform depth throughout the array without interference from each other. In preferred embodiments, the skin penetrating members penetrate the skin to a uniform depth to provide delivery of the substance to the selected depth of the skin and to reduce the risk of leakage when the substance is being delivered. The number of skin penetrating members in the array can vary depending on the dimensions of the skin penetrating member, the substance being delivered, and the depth of penetration. The array may be formed from about 3 to about 100 micro skin penetrating members or it could employ only one or two skin penetrating members. Typically, the array includes between about 5 and 20 skin penetrating members.

While various embodiments have been chosen to illustrate the invention, it will be appreciated by those skilled in the art that various additions and modifications can be made to the invention without departing from the scope of the invention as defined in the appended claims.

What is claimed is:

1. An intradermal delivery device comprising:
    a housing;
    a cartridge removably received in said housing, said cartridge defining an internal reservoir adapted to contain a substance to be delivered to a patient;
    a dispensing member comprising a spring member for contacting said cartridge operable to apply a dispensing pressure to said cartridge wherein said cartridge is collapsible by said dispensing member and said dispensing member is hinged to said housing and is pivotable between an open and closed position, said dispensing member contacting said cartridge when in said closed position to apply said dispensing pressure to said cartridge;
    at least one skin penetrating member, said skin penetrating member having a length sufficient to penetrate the surface of the skin of said patient, said skin penetrating member adapted to be placed in fluid communication with said reservoir for delivering a substance in said reservoir to the patient.

2. The delivery device of claim 1, wherein said skin penetrating member is coupled to said cartridge, said skin penetrating member having a base, an outer end and a passage extending between said base and said outer end, and wherein said base is adapted to be placed in fluid communication with said reservoir.

3. The delivery device of claim 1, wherein said housing has a top edge, a bottom edge and an internal chamber dimensioned to receive said cartridge, said housing further including a coupling member for coupling said device to the skin of the patient.

4. The delivery device of claim 3, wherein said coupling member on said housing is a strap for coupling to the skin of the patient.

5. The delivery device of claim 1, wherein said dispensing member further comprises a cover hinged to said housing, said spring member having a first end fixed to said cover and a second free end.

6. The delivery device of claim 5, wherein said free end of said spring includes an indicator visible through said cover when said spring is in a relaxed position and is not visible through said cover when said spring member is stressed.

7. The delivery device of claim 6, wherein said cover includes a window for viewing said indicator when said spring is in a relaxed position.

8. The delivery device of claim 1, further comprising an indicator for indicating that said substance is dispensed from said cartridge.

9. The delivery device of claim 1, wherein said skin penetrating member has a length of about 50 microns to about 5000 microns.

10. The delivery device of claim 1 wherein said skin penetrating member is one of an array of skin penetrating members, each adapted to be placed in fluid communication with said reservoir.

11. The delivery device of claim 9, wherein said skin penetrating member has a length of about 500 microns to about 3000 microns.

12. The delivery device of claim 11, wherein said skin penetrating member has a length of about 500 microns to about 1000 microns.

13. An intradermal delivery device comprising:
    a housing;
    a cartridge removably received in said housing, said cartridge defining an internal reservoir adapted to contain a substance to be delivered to a patient;
    at least one skin penetrating member, said skin penetrating member having a length sufficient to penetrate the surface of the skin of said patient, said skin penetrating member adapted to be placed in fluid communication with said reservoir for delivering a substance in said reservoir to the patient;
    a piercing member for piercing a wall of said reservoir to allow fluid to flow from said reservoir to said skin penetrating member;

and a cover member defining a dispensing member for said cartridge, said cover member being pivotally connected to said housing and being pivotal between an open position and a closed position, said cover member applying a dispensing pressure to said cartridge when said cover is in said closed position with said cartridge received in said housing wherein said cover member includes a cam surface oriented for actuating said piercing member to pierce said wall of reservoir when said cover is in said closed position.

14. The delivery device of claim 13 wherein said cartridge defines a fluid passageway between said skin penetrating member and the wall of said reservoir where it is pierced by said piercing member.

* * * * *